(12) United States Patent
Bax et al.

(10) Patent No.: US 8,970,141 B2
(45) Date of Patent: Mar. 3, 2015

(54) RESONANT ACTUATOR USING MAGNETIC ACTION FOR A POWER TOOTHBRUSH

(75) Inventors: Pieter Johannes Bax, Eindhoven (NL); Johannes Hotze Bernhard De Vries, Eindhoven (NL); Jurriaan Bernhard Rudolf Leveling, Eindhoven (NL); Gert Westrup, Eindhoven (NL); Sepas Setayesh, Eindhoven (NL); Folkert Vrijburg, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 92 days.

(21) Appl. No.: 13/822,394

(22) PCT Filed: Sep. 19, 2011

(86) PCT No.: PCT/IB2011/054082
§ 371 (c)(1),
(2), (4) Date: Mar. 12, 2013

(87) PCT Pub. No.: WO2012/042427
PCT Pub. Date: Apr. 5, 2012

(65) Prior Publication Data
US 2013/0207575 A1      Aug. 15, 2013

Related U.S. Application Data

(60) Provisional application No. 61/387,505, filed on Sep. 29, 2010.

(51) Int. Cl.
*H02K 33/00* (2006.01)
*H02K 33/18* (2006.01)
(Continued)

(52) U.S. Cl.
CPC ............ *H02K 33/18* (2013.01); *A61C 17/3418* (2013.01); *A61C 17/3445* (2013.01); *H02K 33/16* (2013.01); *H02P 25/027* (2013.01); *H02K 2201/18* (2013.01)
USPC ............................ 318/128; 318/560; 318/268

(58) Field of Classification Search
USPC ........ 318/128, 560, 268, 626, 400.13; 310/38
See application file for complete search history.

(56) References Cited

U.S. PATENT DOCUMENTS

| 5,719,451 | A  | 2/1998 | Cook et al. |
| 7,594,239 | B2 | 9/2009 | Chang et al. |

(Continued)

FOREIGN PATENT DOCUMENTS

| DE | 10355446 A1 | 6/2005 |
| DE | 102006061381 A1 | 6/2008 |

(Continued)

OTHER PUBLICATIONS

Dr. Andrzej M. Pawlak, "Magnets in Modern Rotary Actuators", Industrial Applications Conference, 1995, Thirtieth IAS Annual Meeting, IAS '95, Conference Record of the 1995 IEEE, 1995, vol. 1, pp. 498-504.

*Primary Examiner* — Karen Masih

(57) ABSTRACT

A magnetic actuator system which includes a case (10) and a spindle (22) which extends through the case comprising a magnetizable material such as iron. The actuator further includes a pair of permanent magnet assemblies (14, 16) positioned fixedly within the casing with a longitudinal space there between, wherein the permanent magnet assemblies comprise an alternating plurality of north pole/south magnet sections (18) which extend longitudinally or circumferentially of the actuator. The actuator further includes a coil winding (24) which surrounds the spindle, positioned between the two permanent magnet assemblies. Magnetic pole assemblies (28, 30) attached to the spindle are positioned within the volume encompassed by the permanent magnet assemblies, such that an alternating drive signal produces an oscillating action of the spindle of desired frequency and amplitude.

13 Claims, 5 Drawing Sheets

(51) Int. Cl.
*A61C 17/34* (2006.01)
*H02K 33/16* (2006.01)
*H02P 25/02* (2006.01)

(56) References Cited

U.S. PATENT DOCUMENTS 7,661,653 B2 2/2010 Kondoh
8,022,646 B1 * 9/2011 Sutardja et al. ............... 318/268

FOREIGN PATENT DOCUMENTS

| | | |
|---|---|---|
| EP | 1626483 A1 | 2/2006 |
| EP | 1432106 B1 | 5/2009 |
| JP | 02199325 A | 8/1990 |
| JP | 2006262547 A | 3/2005 |
| WO | 2004047670 A1 | 6/2004 |
| WO | 2007020599 A2 | 2/2007 |
| WO | 2008105393 A1 | 9/2008 |

* cited by examiner

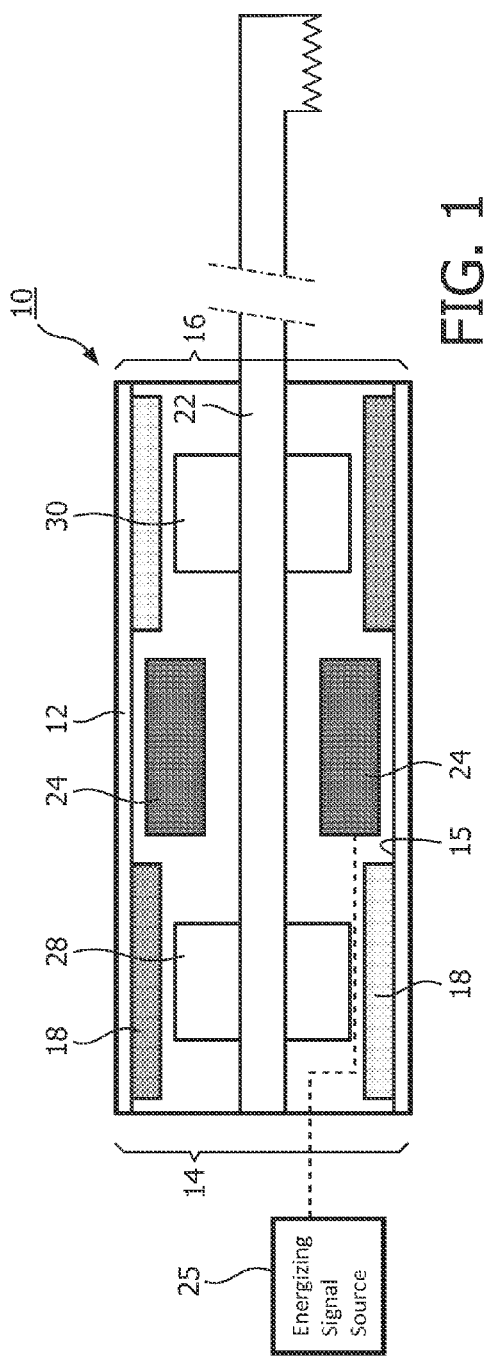
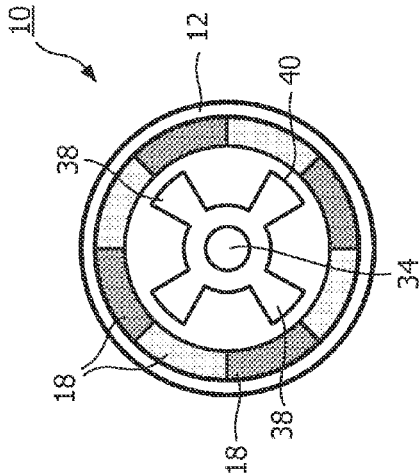

RESONANT ACTUATOR USING MAGNETIC ACTION FOR A POWER TOOTHBRUSH

This invention relates generally to power toothbrushes, and more particularly to an actuator for a power toothbrush using magnetic action to produce an oscillating output shaft motion having a selected angle of motion and frequency.

Electric toothbrushes frequently are arranged to include a resonant actuator to drive a mechanical spring mass system, the action of which in turn produces a desired movement of a brushhead for cleaning of a user's teeth. In a resonant system, the drive frequency of the appliance is set near or approximately equal to the resonant frequency of the spring mass system. A resonant system enables the appliance to work at maximum efficiency for a given power input and is hence desirable for most appliances, including electric toothbrushes.

The overall size of the actuator, as well as the life expectancy of the appliance, are important, but sometimes contradictory, considerations in the design of an electric toothbrush. Attempting to decrease the size of the actuator and hence the size of the appliance, for instance, which is generally desirable, will often have a negative effect on overall function and effectiveness of the appliance, as well as potentially reducing the lifetime of the appliance, since decreasing the size of the resonant spring will generally increase the mechanical stress on the spring, resulting in earlier failure, as well as decreasing the power output of the appliance.

The invention disclosed herein comprises a relatively small diameter actuator for an electric toothbrush which does not affect the function and effectiveness of the toothbrush and/or its operating lifetime.

A magnetic actuator system for a power toothbrush is disclosed, comprising: a case; a spindle of magnetizable material which extends through the case; at least one pair of spaced permanent magnet assemblies fixed in position in the case, wherein the permanent magnet assemblies each comprise a plurality of north pole/south pole magnet sections; a coil winding which surrounds the spindle in the space between the permanent magnet assemblies; a pair of magnet pole assemblies, having a plurality of magnetic pole members attached to the spindle, positioned within a volume surrounded by the permanent magnet assemblies, wherein the magnetic poles extend radially outward from the spindle toward the permanent magnet assemblies; wherein in operation, an energizing signal in the form of a square wave about zero or an alternating current from a source thereof is applied to the coil windings, resulting in an oscillating movement of the spindle at a selected frequency and angle, and wherein the spindle is adapted to receive a brushhead assembly, or a spring assembly which is adapted to receive a brushhead assembly, for cleaning of a user's teeth.

FIGS. 1 and 2 are longitudinal and lateral cross-sectional views of one embodiment of an actuator described herein for rotational action of the actuator spindle.

Figure 3:
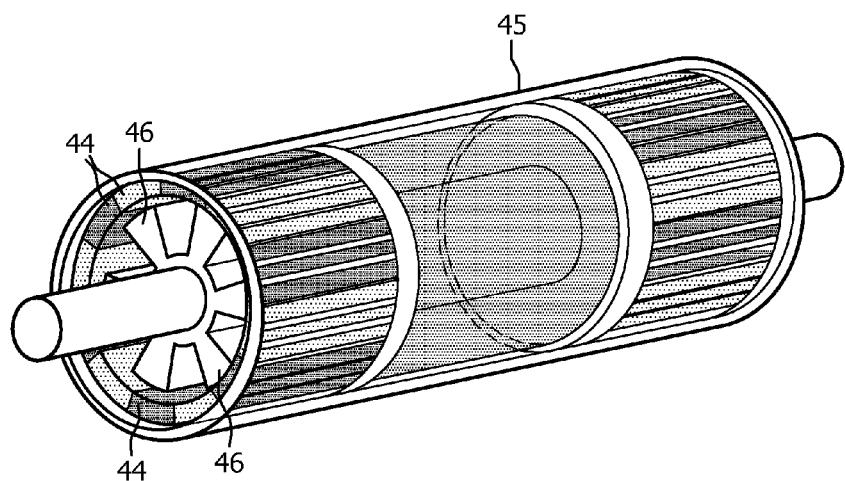
FIG. 3 is a perspective view of another embodiment of the actuator.

FIGS. 1 and 2 show a first embodiment of an actuator 10 which can be used for driving an electric toothbrush with an oscillating rotational action through a selected angle. The actuator 10 includes an elongated, cylindrical case 12 which preferably, but not necessarily, has a small, i.e. slim, diameter, approximately 12-15 mm, with a preferred diameter of 13.6 mm in the embodiment shown. Such a slim actuator case is commercially desirable and the actuator structure described herein makes such a slim configuration possible.

Positioned within case 12, which is preferably made of metal with high magnetic permeability, since the case is part of the magnetic circuit, are two permanent magnet assemblies 14 and 16 in the embodiment shown, positioned near opposing ends of the case 12, attached to the inner surface 15 of case 12. The permanent magnet assemblies comprise magnet sections 18-18 alternating circumferentially between north/south polarity. In the embodiment shown, the magnet sections 18-18 are curved, approximately 10 mm long and 8 mm thick. In the embodiment shown in FIGS. 1 and 2, there are a total of eight magnet sections in each magnet assembly. While the embodiment of FIGS. 1 and 2 show the individual magnetic sections abutting, there could be a gap between successive north/south magnet sections. Permanent magnet assembly 16 is identical to permanent magnet assembly 14, except that the magnet sections of assembly 16 are positioned so that the magnetic poles alternate opposite to that of the magnet sections of assembly 14, i.e. longitudinally a north polarity of a magnet section in assembly 14 is in registry with a south polarity magnet section in assembly 16.

Extending through the middle of case 12 is a spindle 22. Wound around spindle 22 between permanent magnet assemblies 14 and 16 is a cylindrical winding 24, which in the embodiment shown comprises a copper wire coil, the number of turns dependent on several factors, including battery voltage, the desired output power and the actuator size. In the embodiment shown, coil 24 is approximately 16 mm long and approximately 2-3 mm thick. The spindle has a diameter of approximately 4 mm in the area of the coil winding 24, and 2-3 mm in the area of the permanent magnet assemblies 14 and 16.

Actuator 10 also includes two magnetic pole assemblies 28 and 30. The magnetic pole assemblies are secured to spindle 22 and are positioned, respectively, in the areas bounded by the permanent magnet assemblies 14 and 16. The magnetic pole assemblies and the spindle are both made of a magnetic material, for instance, iron. In the embodiment shown, each magnetic pole assembly includes a ring portion 34 adjacent the spindle and a plurality of equally spaced pole members 38. Each pole member increases slightly in width from ring portion 34 to the free end of the pole member. The free ends of the pole members extend almost to the magnet sections. Typically, there is a small gap between them. The free end surface 40 of each pole member is slightly curved in the embodiment shown. The number of pole members 38 in the magnetic pole assembly will be one-half the number of individual magnet sections in the associated permanent magnetic assembly.

The embodiment of FIGS. 1 and 2, as indicated above, show a total of eight magnet sections in each permanent magnet assembly and four equally spaced pole members in each magnetic pole assembly. In other embodiments, however, the number of magnet sections, and hence the number of pole elements in the magnetic pole assemblies, will be different. FIG. 3, for instance, shows an arrangement with a total of 12 magnet sections 44 for each permanent magnet assembly on the inside surface of the case 45, with north and south pole sections alternating around the inside circumference of the permanent magnet assemblies. In the embodiment of FIG. 3, there are a total of six equally spaced pole members 46 to match the 12 magnetic north/south magnet sections. As indicated above, the number of magnet sections, which can vary, will also determine the number of magnetic poles comprising the magnetic pole assemblies.

An energizing signal from a source thereof 25 for operation of the actuator is applied to winding 24 through winding leads (not shown). Referring again to FIGS. 1 and 2 relative to operation, an energizing signal will typically be a square wave (alternating) signal about zero, produced by a full bridge circuit from a DC signal, although an AC signal can also be used. The frequency of the signal can vary, although preferably it is near the resonant frequency of the system. One-half of the square wave energizing signal in the plus direction will result in one of the magnetic pole assemblies being magnetized to north, while the other magnetic pole assembly will be magnetized south. In the unmagnetized state, the individual pole members will each be facing a north/south boundary of the permanent magnet sections in the circumferential direction of the permanent magnet assemblies.

The energizing signal will result in the spindle 22 with the two magnetic pole assemblies rotating to approximately the mid-point of one of the adjacent magnet sections. For instance, if the magnetic pole assembly 28 in FIGS. 1 and 2 is magnetized north while the other assembly 30 is south, the first action will be a rotation of the spindle counterclockwise (FIG. 2), so that the north magnetic poles in assembly 28 will face the south magnet sections by magnetic attraction, and repelled away from the north magnet sections. The south magnetic pole assembly 30 will produce the same counterclockwise rotation because of the complimentary (opposite) position of the permanent magnet sections from permanent magnet assembly 16. The energizing square wave will go back to zero, and then go in the negative direction, resulting in a clockwise rotation of the spindle, with magnetic pole assembly 28 being south and magnetic pole assembly 30 being north. The poles in assembly 28 will move to face the north permanent magnet sections in assembly 14 and the poles in assembly 30 will move to face the south permanent magnet sections in assembly 16.

The repetitive square wave in both directions about zero will result in a back-and-forth oscillation of spindle 22, through an angle which depends upon the number of permanent magnet sections and the corresponding number of magnetic pole elements. For instance, in an embodiment with a total of 12 magnet sections in each permanent magnet assembly, the angle of oscillation will be approximately ±15° theoretically, slightly less in actuality, which is an effective brushing stroke for cleaning teeth. A suitable range could be 9-16°.

In operation, the actuator has very preferred magnetic positions. The user can rotate the brush spindle into a preferred initial (at rest) angular position. The spindle of the actuator can be oriented in several different positions. The magnetic cogging torque becomes negative for a positive rotation of the spindle and positive for a negative rotation. The cogging torque thus can be used to accomplish the spring function. In such a case, mechanical springs can be omitted, since the spring function is realized by the magnetic cogging effect, in effect a magnetic spring.

In one arrangement, a brushhead could be attached directly on one end of the spindle, to produce an effective brushing action, with the magnetic spring being sufficient to produce the desired action. In other cases, the magnetic spring action of the actuator may not be strong enough to produce an effective brushing force. In those such cases, the spindle of the actuator can be used to drive a separate mechanical spring mass system.

Figure 4:
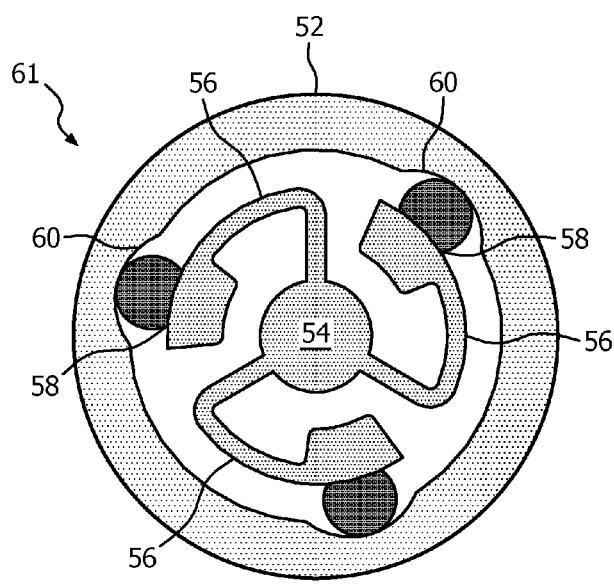
FIG. 4 is an end view of a ball spring which can be used with the actuator of FIG. 35.
Figure 5:
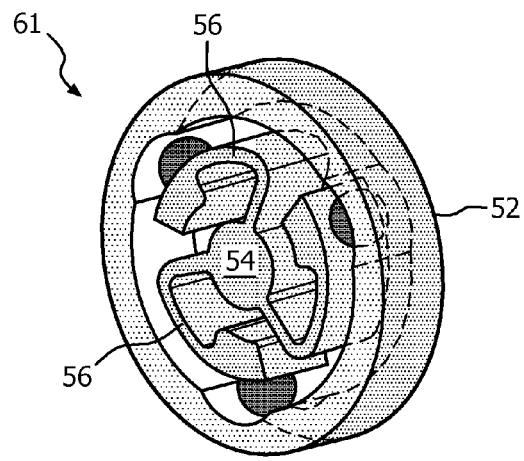
FIG. 5 is a perspective view of the ball spring of FIG. 4.
Figure 6:
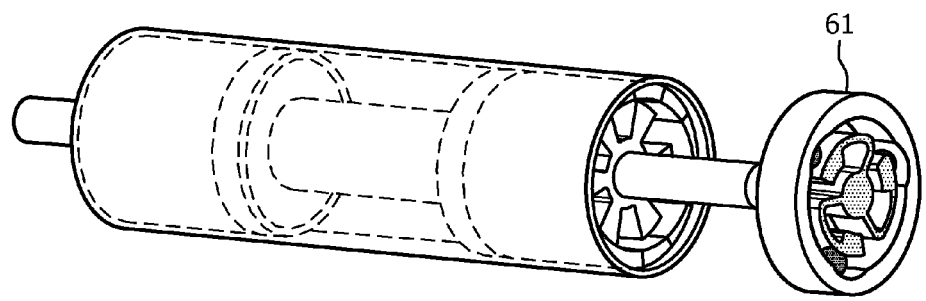
FIG. 6 is a perspective view of the actuator/ball spring combination.

Such a separate spring mass system could include a leaf or helical spring, which are conventional spring mass arrangements, or a ball spring assembly 61, such as shown in FIGS. 4 and 5. FIG. 6 shows a ball spring arrangement of FIGS. 4 and 5 in combination with the actuator of FIG. 3. The ball spring assembly includes a narrow, ring-like outer stator portion 52, which in the embodiment shown has the same exterior diameter as case 12. The thickness of the outer portion can vary. The ball spring assembly 61 also includes an inner moving part which includes a center member 54 which is secured to or a part of the spindle from the actuator. Extending outwardly from the center member 54 are a plurality of arms 56. The number of arms, preferably equally spaced, can vary, although three arms provide reliable and effective results. Each arm extends directly outwardly toward outer portion 52 from center member 54 and then curves to follow the curved inner surface of the outer portion 52. At the end of each arm is a cavity portion 58, which is in registry with a shallow cavity or dip 60 in the inner surface of the outer portion. Small balls are positioned between each cavity 58 and each cavity/dip 60. The arms of the moving part provide a pre-stress force. This particular arrangement can act as a spring in both the tangential and the axial directions.

Figure 7:
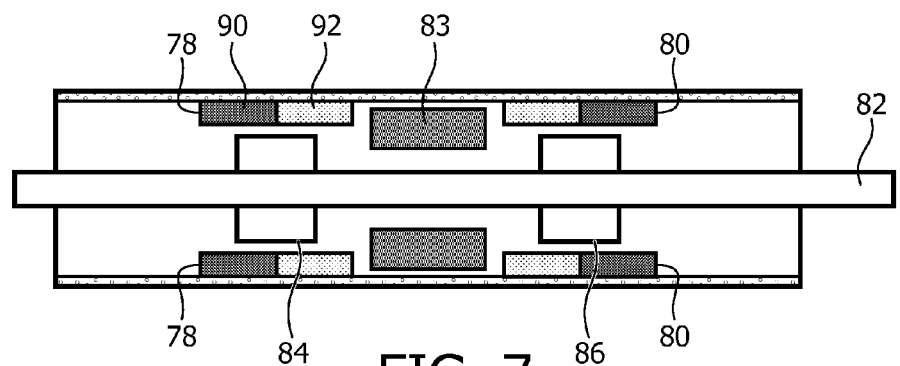
FIGS. 7-9 are longitudinal cross-sectional views of additional embodiments of the actuators, for axial motion of the actuator spindle.

FIG. 7 shows an actuator with axial movement, rather than the rotational movement of the above embodiments. It includes two spaced permanent magnet assemblies 78 and 80, a spindle 82 and a coil winding 83 therebetween, and two magnetic pole assemblies 84 and 86, attached to the spindle 82, inside of the permanent magnet assemblies. The permanent magnet assemblies are arranged axially (circumferentially) in which the north/south boundaries of the magnet sections extend circumferentially, instead of longitudinally for the rotational actuator. For instance, permanent magnet assembly 78 includes a north pole magnet section 90 and an adjacent south pole magnet section 92. In the embodiment shown, the magnet sections 90 and 92 extend circumferentially around the entire casing, and like the magnet sections 44, are approximately 1 mm thick. It is possible that the magnet sections may be segmented around the circumference, i.e. a plurality of magnet sections. The individual magnet segments can either abut each other or be separated by a small gap.

The other permanent magnetic assembly 80 is similar in arrangement, except that the north and south pole sections are reversed, such that the north magnet sections of both permanent magnet assemblies are on the outside position, while the south magnet sections are in the inside position, as shown in FIG. 7.

The magnetic pole assemblies in the embodiment of FIG. 7 could be a solid disc-like element, or it could be a series of spaced individual poles. While each permanent magnet assembly is shown in FIG. 7 to have one north and one south section, there could be a greater number than just one north and one south pole section spaced longitudinally along the case.

In operation of the actuator relative to its axial movement, energizing the winding 83 with a square wave having plus and minus excursions or an alternating current signal, will for instance magnetize the magnetic pole assembly 84 to north, and opposing magnetic pole assembly 86 to south. This will result in a movement of spindle 82 initially to the left (axially) as the magnetic poles 84 and 86 will tend to line up with the opposing pole section of the permanent magnet assembly. When the energizing signal moves to its opposing excursion, the spindle 82 will move first back to a neutral position and then to the right, when the magnetic pole assembly 84 is magnetized to south and the opposing magnetic pole assembly 86 is magnetized to north. As the energizing signal continues, the spindle will move back and forth longitudinally (axially) along the case.

Figure 8:
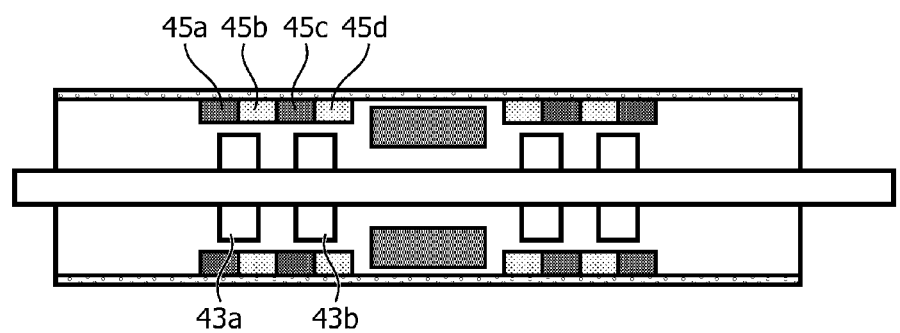
Figure 9:
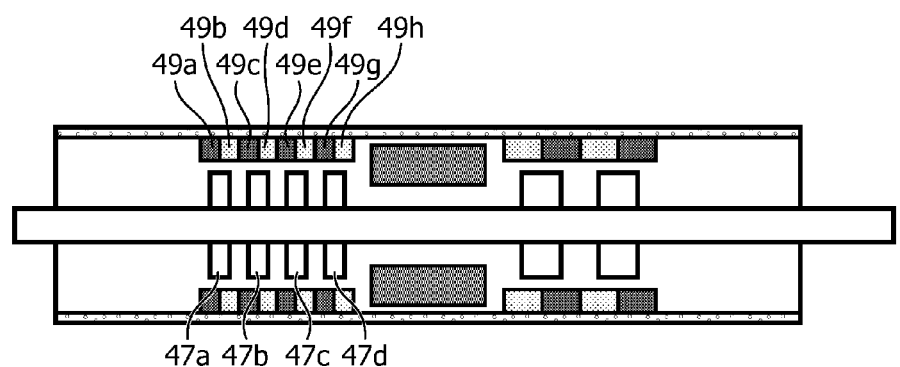

In the event of additional north-south magnet sections, the magnetic pole assemblies will include a series of separate magnetic pole members, spaced to coincide longitudinally with the abutting north/south lines of the magnet sections. FIGS. 8 and 9 show two such arrangements.

FIG. 8 shows an embodiment which produces a relatively small axial (longitudinal) stroke. There are two pole members for each magnetic assembly, which include four circumferential magnet sections. For simplicity of illustration, the pole members 43a-43b are specified relative to one magnetic assembly with magnet sections 45a-45d. The width of each pole member is half of the embodiment of FIG. 7. The operating range is reduced by a factor of 2, but the actuator force is doubled.

FIG. 9 shows an embodiment for axial movement with four pole members for each magnetic assembly, and a total of eight separate circumferential magnet sections. For one magnetic assembly, the four pole members are labeled 47a-47d and the eight magnet sections are labeled 49a-49h for illustration. The actuator range is further decreased again by a factor of two and the actuator force further increased by a factor of two relative to the embodiment of FIG. 8. As with other embodiments, the number of pole members is one-half the number of magnet sections.

Figure 10:
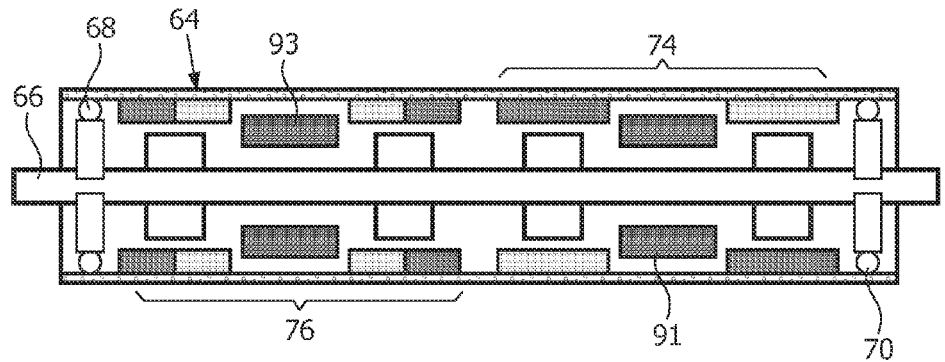
FIG. 10 is a longitudinal cross-sectional view of an actuator capable of producing both axial and tangential motion of the actuator spindle.

FIG. 10 shows an actuator configuration which is capable of producing both axial and rotational movement of the spindle. It includes a case 64, a central spindle 66 and ball spring assemblies 68 and 70, similar to that shown in FIGS. 4 and 5, at both ends of the case. The portion of the actuator referenced at 74 produces the rotational movement and is identical to that shown in FIGS. 1 and 2. The portion of the actuator referenced at 76 produces the axial movement, and is identical to that shown in FIG. 7.

An energizing signal applied to winding 91 of actuator portion 74 will produce a rotational movement (like that described for FIGS. 1 and 2 above). Actuator portion 76 can be energized by a signal applied to winding 93 which is completely separate from that applied to actuator portion 74, which typically will be preferred, or the signal could be the same. This arrangement will produce axial movement of the brushhead as well as rotational movement of the brush. Further, using different frequencies for the energizing signals for the two actuator portions will produce different brushing patterns.

The actuator described herein can also include a control system for stabilizing the stroke of the brushhead. In this arrangement, referring to FIG. 11, the actuator includes a sensing coil 94 in addition to the actuator coil 95. In operation, the sensing coil receives a magnetic flux induced from the permanent magnet assemblies. The flux produced by the permanent magnets will vary, depending upon the position of the spindle. The induced flux in the sensing coil 94 produces a voltage which is related to the stroke speed of the moving part of the actuator.

Figure 11:
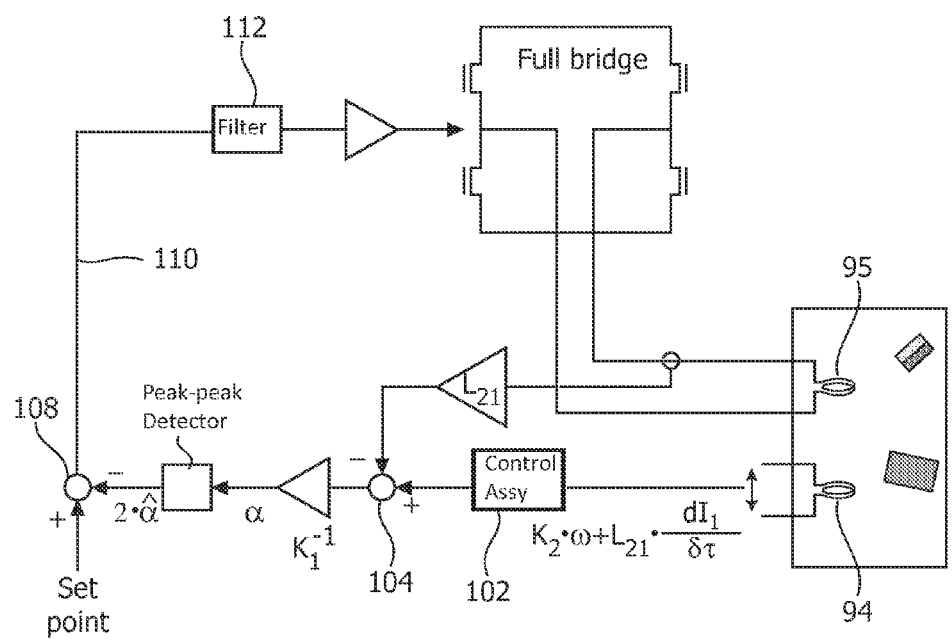
FIG. 11 is a block diagram of a sensing coil/feedback arrangement for control of the angular movement/stroke of the actuator system.

The voltage also contains components which result from the interaction of the sensing coil and the actuator coil, which basically act as a two-winding transformer. In order to obtain an accurate indication of the stroke information (angular speed), the undesired component must be eliminated. If the current in the sensing coil 94 is zero, then the voltage will consist of the actuator coil back emf voltage and a transformer voltage according to the following formula:

$$K_2 \cdot \omega + L_{21} \cdot \frac{dI_l}{dt}$$

where $K_2$ is the actuator constant in the sensing coil and $L_{21}$ is the mutual conductance between the sense coil and the actuator winding. This amount, $$L_{21} \cdot \frac{dI_l}{dt},$$

must be eliminated. In FIG. 11, the voltage output of sensing coil 94 is as indicated above:

$$K_2 \cdot \omega + L_{21} \cdot \frac{dI_l}{dt}.$$

This voltage is integrated at 102 and then applied to one input of a plus/minus comparator 104, the other input being $L_{21} \times l_1$, where $l_1$ is obtained from the actuator coil. After further amplification and peak-to-peak detection, a voltage $2 \cdot \text{æ}$ representative of the brush stroke is produced. This value is applied to one input of a plus/minus comparator 108. The desired stroke, represented by a peak-to-peak voltage, is applied at the other input, with any difference being applied on line 110 to a filter 112 and then back to the full bridge, to maintain the desired stroke value, by changing the frequency or duty cycle of the driving signal.

Accordingly, an actuator has been disclosed which is suitable for use as an electric toothbrush. The actuator structure has significant advantages, since it permits a small appliance to have a desirable small, i.e. slim, cross-sectional shape, without sacrificing effectiveness and product life.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. A magnetic actuator system for a power toothbrush, comprising:
 a case;
 a spindle of magnetizable material which extends through the case;
 at least one pair of spaced permanent magnet assemblies fixed in position in the case, wherein the permanent magnet assemblies each comprise a plurality of north pole/south pole magnet sections wherein the north pole/south pole magnet sections of one permanent magnet assembly oppose the north pole/south pole magnet sections of the other permanent magnet assembly;
 a coil winding which surrounds the spindle in the space between the permanent magnet assemblies;
 a pair of spaced magnet pole assemblies, each having a plurality of magnetic pole members, attached to the spindle, positioned within a volume surrounded by the permanent magnet assemblies, wherein the magnetic pole members extend radially outward from the spindle toward the permanent magnet assemblies and wherein one magnet pole assembly is magnetized north while the other magnet pole assembly is magnetized south;

wherein in operation, an energizing signal in the form of a square wave about zero or an alternating current from a source thereof is applied to the coil windings, resulting in a magnetic interaction between the magnet coil assemblies and the spaced permanent magnets assemblies, providing an oscillating movement of the spindle at a selected frequency and angle, and wherein the spindle is adapted to receive a brushhead assembly or a spring assembly adapted to receive a brushhead assembly, for cleaning of a user's teeth.

2. The actuator system of claim 1, including a ball spring secured to or part of the spindle.

3. The actuator system of claim 1, wherein the actuator is arranged to function in operation as a magnetic spring due to cogging torque of the actuator.

4. The actuator system of claim 1, wherein the north pole/south pole magnet sections alternate circumferentially around the interior of the case.

5. The actuator system of claim 1, wherein the north pole/south pole magnet sections alternate longitudinally along the case.

6. The actuator system of claim 1, including two sets of at least one pair of permanent magnet assemblies, wherein the north pole/south pole magnet sections in one set of permanent magnet assemblies alternate circumferentially about the interior of the case and wherein the north pole/south pole magnet sections in the other set alternate longitudinally along the case.

7. The actuator system of claim 4, wherein each permanent magnet assembly includes at least eight magnet sections, with alternating north and south poles, and wherein the magnetic pole assemblies each comprise a center section and half as many equally spaced magnetic pole members as magnet sections extending outwardly therefrom.

8. The actuator system of claim 5, wherein each permanent magnet assembly includes at least four magnet sections, with alternating north and south poles, and half as many magnetic pole members as magnet sections spaced along the spindle within the volume encompassed by the permanent magnet assemblies.

9. The actuator system of claim 1, wherein the spindle and the magnetic pole assemblies are made from iron.

10. The actuator system of claim 1, wherein the spindle has a greater diameter in the portion thereof which is in registry with the coil winding than in the portions thereof which are in registry with the permanent magnet assemblies.

11. The actuator of claim 1, wherein the case has a diameter in the range of 12-15 mm.

12. The actuator of claim 1, wherein the selected angle is within the range of 9-16°.

13. The actuator system of claim 1, including a sensing winding in the vicinity of the coil winding, wherein movement of the permanent magnet assemblies produces a flux which induces a voltage in the sensing winding dependent upon the position of the sensing coil relative to the permanent magnet assemblies, and wherein the actuator system includes a control assembly for processing the voltage signal from the sensing winding to resolve a voltage which is due only to the flux from the permanent magnet assemblies and for comparing that voltage against a standard value and for thereafter changing the frequency or duty cycle of the driving signal to produce a spindle stroke of the spindle of desired magnitude and/or angle.

* * * * *